US00PP13069P2

(12) United States Plant Patent
Simmen

(10) Patent No.: US PP13,069 P2
(45) Date of Patent: Oct. 8, 2002

(54) DOGWOOD TREE NAMED 'ETERNAL DOGWOOD'

(75) Inventor: Pierre W. Simmen, Fuquay-Varina, NC (US)

(73) Assignee: Caroline Domenig, Kernersville, NC (US); a part interest ( * ) Notice: Subject to any disclaimer, the term of this patent is extended or adjusted under 35 U.S.C. 154(b) by 0 days.

(21) Appl. No.: 09/873,697

(22) Filed: Jun. 4, 2001

Related U.S. Application Data

(63) Continuation-in-part of application No. 09/404,213, filed on Sep. 23, 1999, now abandoned.

(51) Int. Cl.[7] ..... A01H 5/00
(52) U.S. Cl. ..... Plt./220
(58) Field of Search ..... Plt./220, 216

*Primary Examiner*—Bruce R. Campell
*Assistant Examiner*—June Hwu

(57) ABSTRACT

A very hardy dogwood tree which produces many large multiple flower bracts (12 to 20 bracts) so that the tree appears to be a mass of blooms. The blooming season for this tree can typically last up to two weeks longer than a conventional dogwood's blooming season. The leaves are large and healthy green in color.

5 Drawing Sheets

BOTANICAL CLASSIFICATION

*Cornus florida* 'Eternal Dogwood'.

BACKGROUND OF THE INVENTION

A dogwood plant providing the basis of my new discovery was found at my previous home at 306 Skiles Heights, Thomasville, Davidson County, N.C. The location of discovery was a Wisteria growing area in back of the property. A small tree about 1 meter in height appeared to have multiple flowering blossoms (12 to 16 bracts). I began nurturing the tree and later propagated branches of that tree at the same location selecting branches with the largest quantity and size of flowering bracts. Branches were marked in spring, then cut and placed in moist potting soil in the late summer.

These trees bloomed 3 years later with 12 to 16 bracts. Many blooms had signs of 20 bracts but they failed to open. At 4 years old of age, they began to produce blooms with 12 to 20 bracts. By the fifth year most blooms had 16 to 20 bracts.

Before moving to my new home at 620 Lakewood Road, Wake County, Fuquay-Varina, N.C., I destroyed all but one tree, and that saved tree was planted at my new home. This tree is now documented as the parent tree. The parent tree is healthy and now yields 12 to 20 bracts per flora (most are 16 to 20 bracts).

BRIEF SUMMARY OF THE INVENTION

The most distinguishing characteristics of this tree are the blooms with 12–20 bracts and the uniform white color of its flowers. In contrast, the 'Daybreak' dogwood (U.S. Plant Pat. No. 6,320) normally has blooms with 4 bracts, and the 'Phillips Pink No. 1' double dogwood (U.S. Plant Pat. No. 8,518) is pink and has blooms with 8 bracts. I have chosen to identify my new dogwood plant as 'Eternal Dogwood' for purposes of identification and use in the trade. Color, when referenced, is compared with Royal Horticultural Society Colour Chart.

DETAILED BOTANICAL DESCRIPTION

Figure 1:
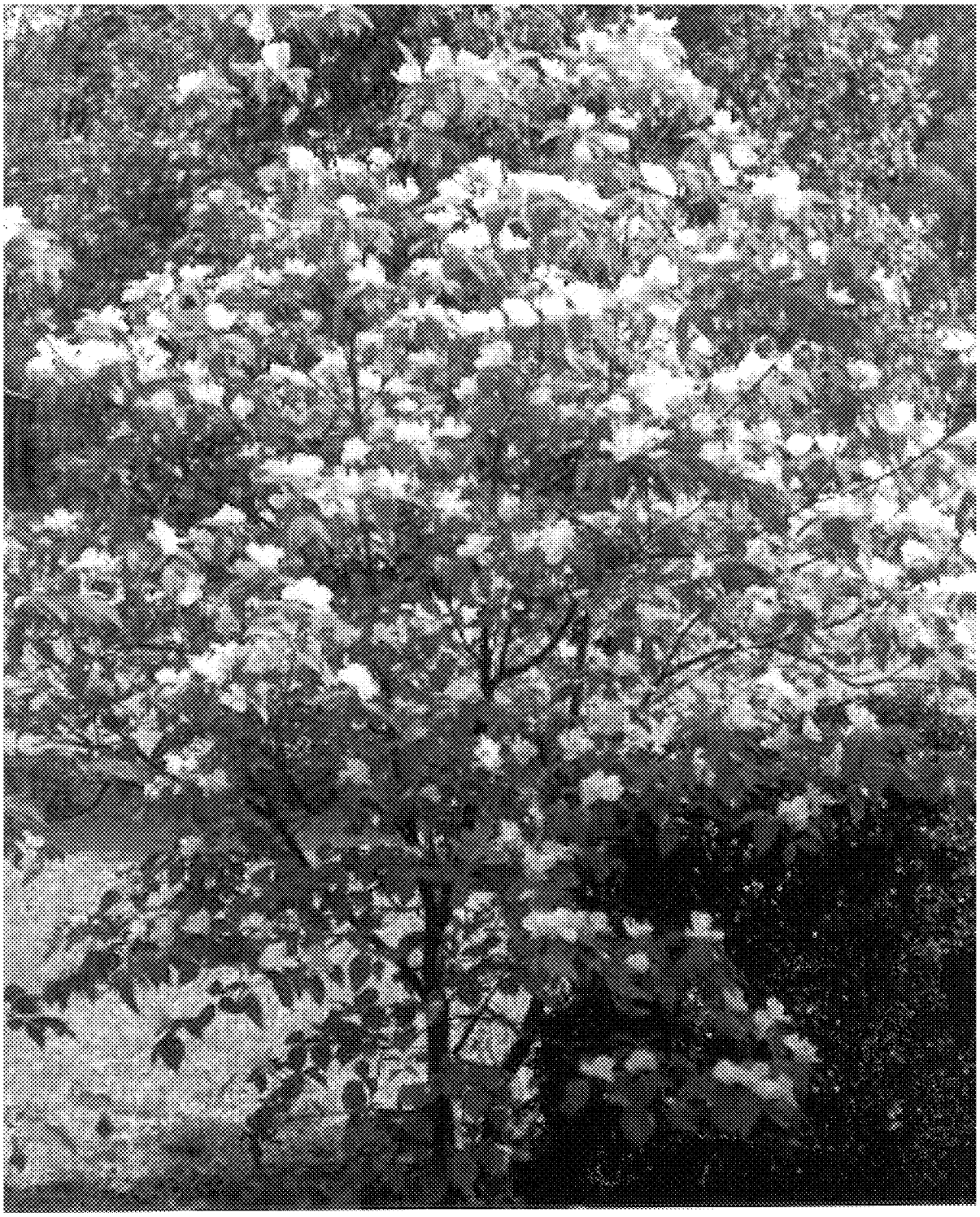
FIG. 1 is a view of the plant at maturity in tree form.
Figure 2:
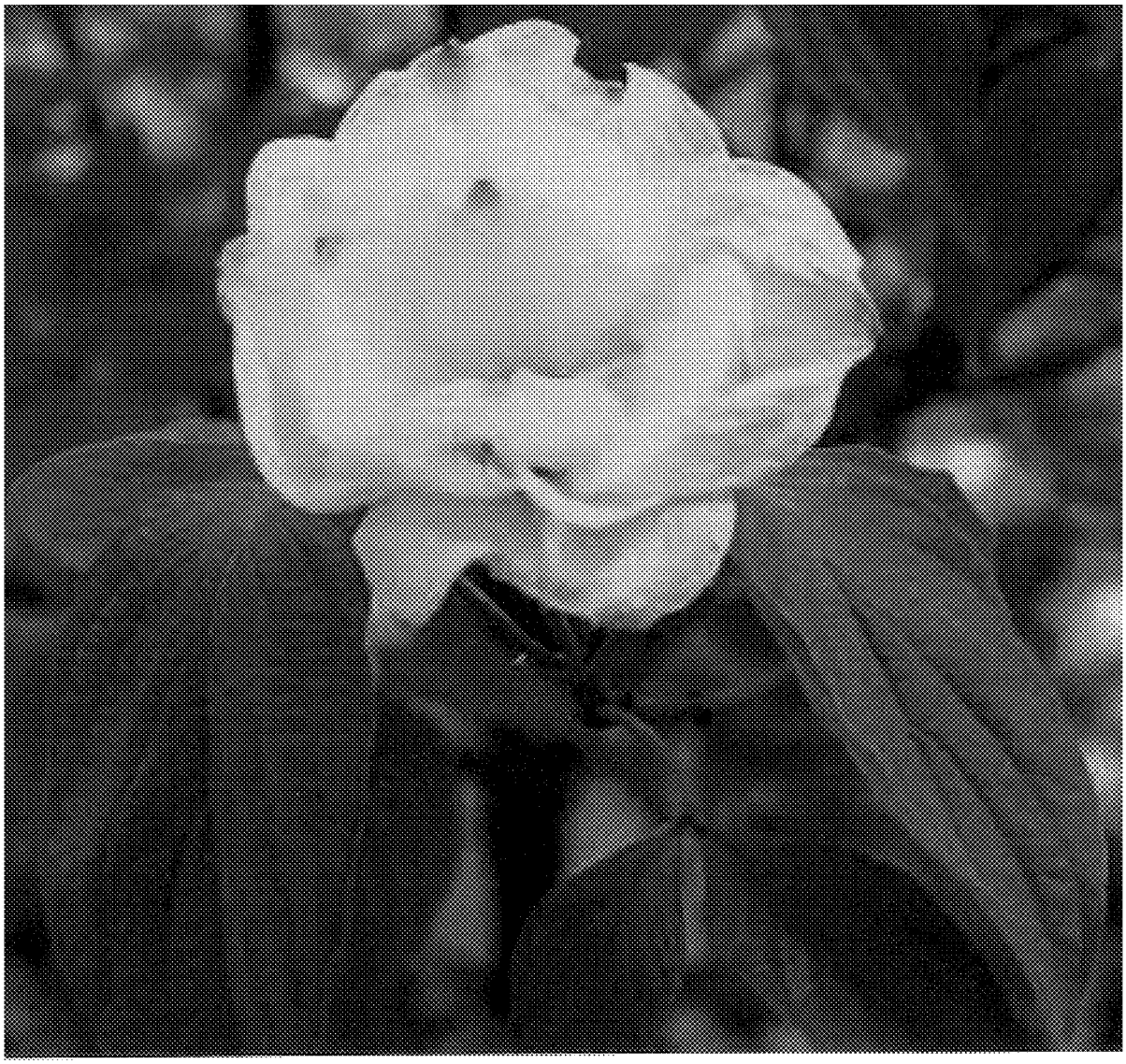
FIG. 2 is a view of a single bloom of the plant fully opened together with a leaf cluster showing the color and shape of the leaves and flower bracts in detail.
Figure 3:
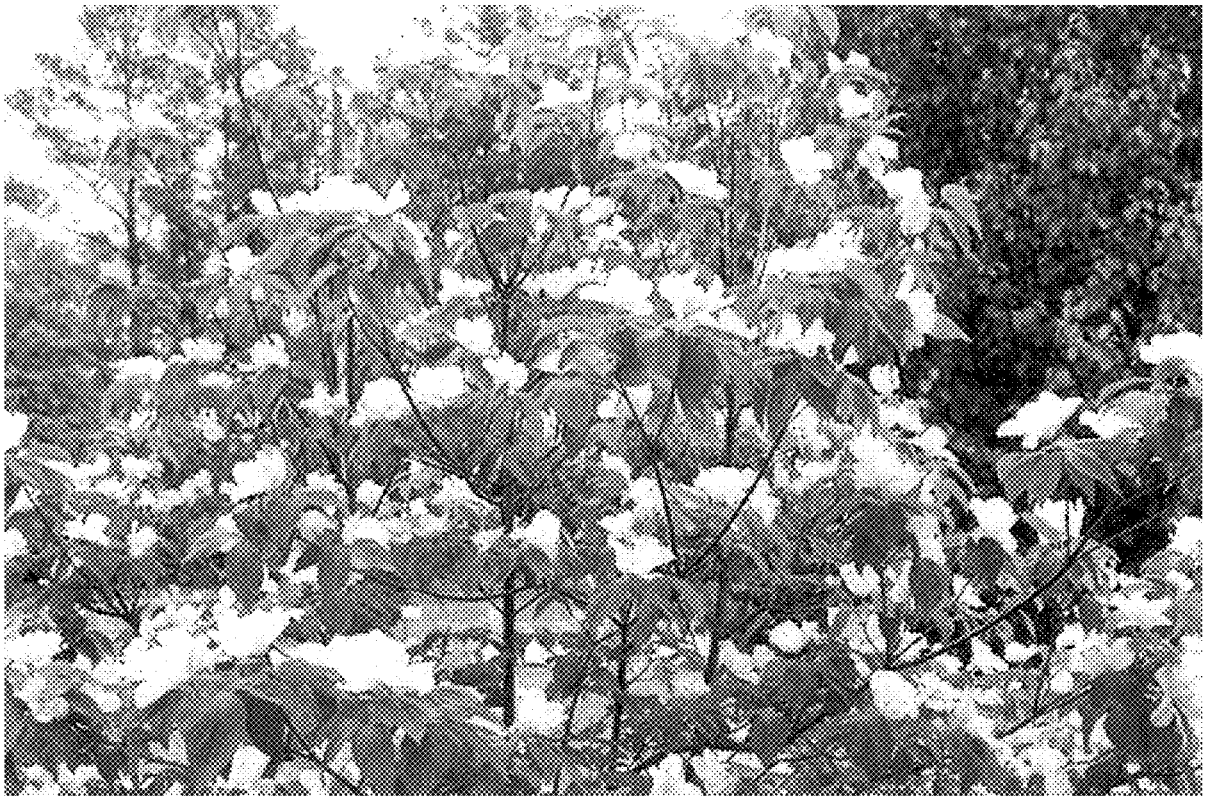
FIG. 3 is an intermediate view of the formation of the flora, leaves and branches in the uppermost part of the tree.
Figure 4:
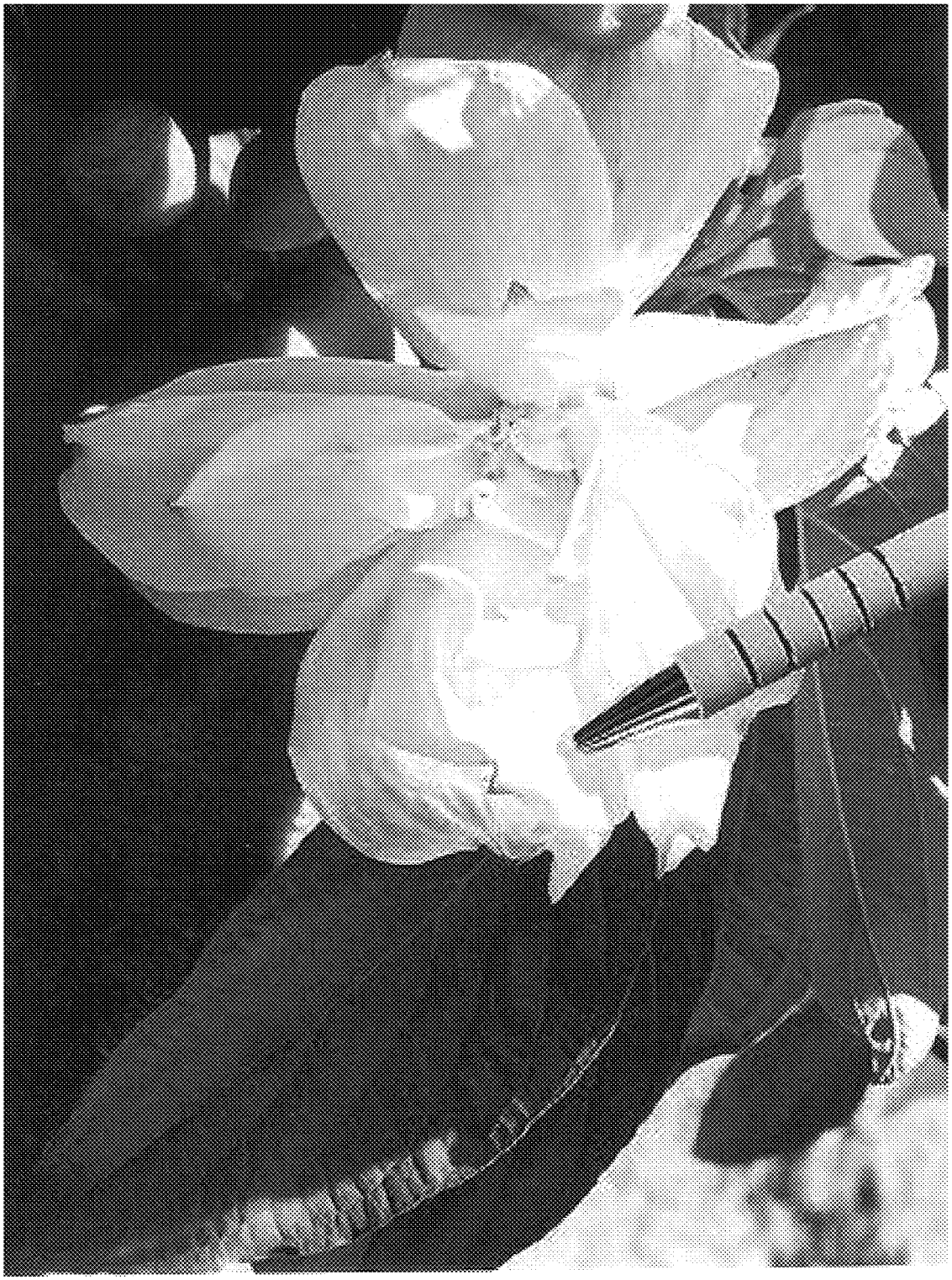
FIG. 4 is a close-up view of the floral bracts and surrounding leaves, opened to better view the bloom interior.
Figure 5:
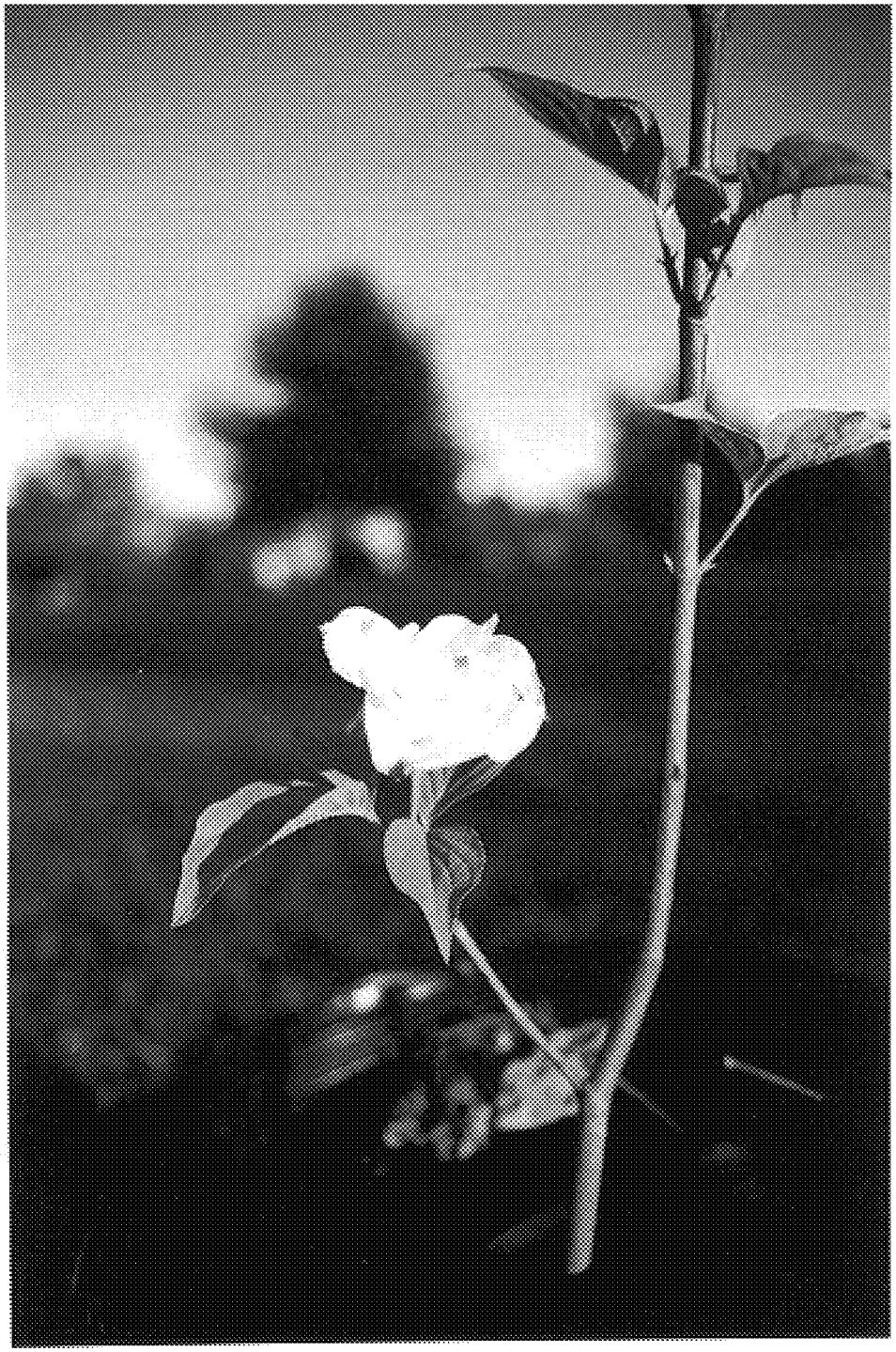
FIG. 5 illustrates a two-year old 60 cm high tree with a single bloom.

This invention relates to a flowering dogwood plant (related to *Cornus florida*) which I discovered as a chance seedling as previously described. Most flowers of the tree of at least 5 years of age yield 16 to 20 bracts per blossom. There are no less than 12 bracts per normal bloom. Blooms are large and numerous and virtually blanket the tree. A normal *Cornus florida* has four bracts per blossom and a double *Cornus florida* has eight bracts per blossom.

The tree has no seeds as the flowering bracts grow one behind another until the end of blooming season. As with all asexually produced plants, successive generations are assisted. Successive generations grown from branches in moist soil in Fuquay-Varina, N.C. have never lost their vigorous growth or flora characteristics and reproduced true to type (large dark green leaves with 12 to 20 bracts per flora). Four commerical growers (one in Winston Salem, N.C. and three in various parts of central Tennessee) under my direction have also asexually reproduced these trees by T budding and cultivating branches in moist soil. Several trees (about 60 cm tall and 2 years old) have bloomed with 12 to 16 bracts per flora and are expected to have mostly blooms of from 16 to 20 bracts when they grow taller.

Tree: Medium, oval, spreading, dense, and hardy. Grows to a height of about 3 to 4 meters in 4 to 5 years with a spread of from 1.25 to 1.6 meters. The tree is approximately 7 years, 8 months old and is shorter now (from 2 to 3.25 meters tall) because of branch removal by growers for asexual reproduction.

*Branches.*—Mature limbs grow at about a 30-degree angle from the trunk. Young branches: Slender, smooth, RHS Color 199B greyed-brown group. Old branches: Medium, smooth, RHS Color 201D greyed group.

*Trunk.*—Stocky, diameter after 5 years about 11 to 13 cm measured 1 meter from ground.

*Bark.*—Medium texture, smooth when young, becomes scaly with age, Color RHS Color 199D greyed-brown group.

*Leaves.*—Medium thickness, abundant, smooth edges, elliptical, with base broadly cuneate, sometimes mildly oblique, and tip abruptly acuminate, three to five leaves per cluster; Length — 115 mm to 135 mm; Width 85 mm–100 mm; Lower leaf surface — matt, veined typical of species, RHS Color 146C yellow-green group; Upper leaf surface — glossy, veined typical of species, RHS Color 137B green group; Lenticels — few, small; Petiole — short, slender, approximately 60 mm long; Glands — none; Stipules — none.

*Fruit.*—None.

*Fragrance.*—None.

*Flower buds.*—Very hardy; Size — width 5.5 mm to 8 mm, height 5.5 mm to 8.5 mm; Color RHS Color 150 D yellow green group; Shape globose; Anther — none; Pistil — none; Stamen — none; Blooming habit — first blooms usually occur a week after other well known *Cornus florida* dogwoods in the area bloom; regular yearly flowering blooms last about 14 to 18 days longer than nearby *Cornus florida* dogwoods; the plant bears flowers at an early age (as early as two years); Quantity — abundant; Bracts — 12 to 20 bracts (16 average); Bract tip — Apical notches which are 30 mm to 90 mm deep, RHS Color 150C yellow green group; Bract base — comparable to *Cornus florida;* Bract surface — matt, smooth, soft, RHS Color 157D green white group; Bract margin — smooth; When the floral bracts are fully expanded, the diameter from tip to tip is 130 mm to 160 mm; First largest four bracts from tip to tip is 65 mm to 80 mm, width 50 mm to 65 mm; Second four bracts — length 50 mm to 60 mm, width 25 mm to 45 mm; Third four bracts — length 70 mm to 90 mm, width 10 mm to 25 mm; Fourth four bracts — length 15 mm to 20 mm, width 5 mm to 10 mm; Fifth four bracts — length 3 mm to 5 mm, width 3 mm to 5 mm.

*General.*—Fully winter hardy in Zone 7, per U.S. Department of Agriculture's Hardiness Zone Map (0 Degrees to 10 degrees F.); Growers indicate that the tree is highly resistant to fungus and mildew and very drought-resistant; No testing on pest susceptibility has yet been conducted.

I claim:

1. A new and distinct variety of Dogwood tree substantially as shown and described herein, characterized particularly as to novelty by its large number of flower bracts per blossom (12 to 20 bracts) and its overall white bloom coloration.

* * * * *